(12) United States Patent
Harper

(10) Patent No.: US 8,658,182 B2
(45) Date of Patent: Feb. 25, 2014

(54) PHYTOPLANKTON BASED NUTRACEUTICALS

(76) Inventor: Tom G. Harper, Nanaimo (CA)

( * ) Notice: Subject to any disclaimer, the term of this patent is extended or adjusted under 35 U.S.C. 154(b) by 846 days.

(21) Appl. No.: 11/375,855

(22) Filed: Mar. 15, 2006

(65) Prior Publication Data

US 2006/0207168 A1    Sep. 21, 2006

Related U.S. Application Data

(63) Continuation-in-part of application No. 11/081,851, filed on Mar. 15, 2005.

(51) Int. Cl.
*A61K 36/02* (2006.01)

(52) U.S. Cl.
USPC .................................... 424/195.17

(58) Field of Classification Search
None
See application file for complete search history.

(56) References Cited

U.S. PATENT DOCUMENTS

| | | | |
|---|---|---|---|
| 4,023,734 A | | 5/1977 | Herve |
| 4,253,271 A | * | 3/1981 | Raymond ........................ 47/1.4 |
| 4,417,415 A | * | 11/1983 | Cysewski et al. ................ 47/1.4 |
| 4,581,233 A | | 4/1986 | Herve |
| 4,824,673 A | | 4/1989 | Herve |
| 4,897,266 A | | 1/1990 | Herve |
| 5,547,997 A | | 8/1996 | Kludas |
| 6,346,252 B1 | | 2/2002 | Moigne |

FOREIGN PATENT DOCUMENTS

JP          06098786 A    *    4/1994

OTHER PUBLICATIONS

Sunlit Ocean (Euphotic) Zone Animal Printouts. Internet Archive Date: Aug. 31, 2004 [Retrieved from the Internet on: Mar. 21, 2008]. Retrieved from: http://web.archive.org/web/*/http://www.enchantedlearning.com/biomes/ocean/sunlit/.*
Zhang et al. "Sustainable, High-Yielding Outdoor Mass Cultures of *Chaetoceros muelleri* var. subsalsum and *Isochrysis galbana* in Vertical Plate Receptors". Marine Biotech. vol. 5 (2003) 302-310.*
Haug et al. "Polysaccharides of Marine Diatoms with Special Reference to *Chaetoceros* Species" Marine Biol. vol. 34 (1976) 217-222.*

* cited by examiner

*Primary Examiner* — Amy L Clark
(74) *Attorney, Agent, or Firm* — Dunlap Codding, P.C.

(57) ABSTRACT

A method of producing a phytoplankton extract includes obtaining seawater including phytoplankton. The seawater is stored in a tank and circulated within the tank. Air is mixed with the seawater. The phytoplankton is autolysed. The phytoplankton is collected. A compound includes an autolysed phytoplankton taken from an algae paste. The autolysed phytoplankton can be a powder or a liquid.

13 Claims, 2 Drawing Sheets

PHYTOPLANKTON BASED NUTRACEUTICALS

This is a continuation-in-part of Application No. 11/081,851, filed Mar. 15, 2005, entitled "PHYTOPLANKTON BASED NUTRACEUTICALS." The entire disclosure of the prior application is hereby incorporated by reference herein in its entirety.

FIELD OF THE INVENTION

This invention relates to algae extracts in general, and more particularly to nutraceuticals made from phytoplankton.

BACKGROUND OF THE INVENTION

It is known in the art that some algae have medicinal properties. For example, U.S. Pat. No. 6,346,252 to Moigne discloses a method of obtaining an antibacterial extract from the algae known as *Bonnemczisoniacea*. U.S. Pat. No. 4,581,233 to Hervéet al. discloses drugs based on extracts of the brown algae known as *Bifurcaria Rotunda, Fucus Vesiculosus, Ascophyllum Nodosum, Pelvetia Canaliculata* and the red algae known as *Delesseria Sanguinea*.

The above-mentioned patents contain examples of extracts derived from seaweeds or macroalgae, which are multicellular and usually visible to the naked eye. Although seaweeds and phytoplankton both belong in the Kingdom Protista, they are in separate Phyla.

Marine phytoplankton, also known as marine microalgae, comprises hundreds of species of photosynthetic, unicellular organisms belonging to the Kingdom Protista. Temperate coastal waters, such as those along the province of British Columbia in Canada, are highly productive and support a diverse array of microalgae species from numerous Classes, including primary producers called diatoms (Class Bacillariophyceae). Every spring, when conditions of light, nutrients, and mixing are optimal for growth, diatoms grow rapidly in the euphotic zone of the ocean (the upper 20 meters). This event is known as the "spring bloom". During this period, many species take advantage of the enhanced conditions but generally three diatom genera are the most successful *Skeletonema, Thalassiosira*, and *Chaetoceros*.

BRIEF SUMMARY OF THE INVENTION

A method of producing a phytoplankton extract includes obtaining seawater including phytoplankton. The seawater is stored in a tank. The seawater is circulated within the tank. Air is mixed with the seawater. The phytoplankton is autolysed. The phytoplankton is collected.

In another aspect of the invention, a composition consists essentially of phosphoric, soluble potash, boron, chelated copper, chelated iron, chelated manganese, molybdenum, chelated zinc, and ethylenediamine.

In a further aspect of the invention, a compound includes an autolysed phytoplankton taken from an algae paste.

In a further aspect of the invention, an apparatus includes a mixing chamber to be connected to a bottom of a tank. A support structure is attached to the mixing chamber. The support structure spaces the mixing chamber from the bottom of the tank. A line is connected to an air source. The line is attached to the mixing chamber and arranged to inject air into the mixing chamber.

These and other features of the present invention will become more fully apparent from the following description, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE INVENTION

Figure 1:
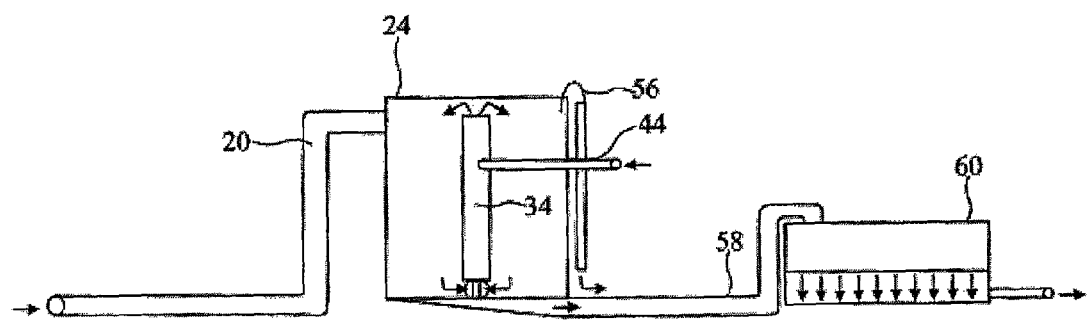
FIG. 1 is a schematic view of a system of the present invention.

To efficiently produce phytoplankton in sufficient numbers and diversity of species and in a controlled environment, it is best to recreate the "spring bloom" conditions found in nature. Phytoplankton taxonomy is based on cell morphology (shape), surface ornamentation, color, and food reserves. Most often identification of phytoplankton is through a compound or inverted light microscope at 250-400x magnification. For some species it is necessary to observe details through an electron microscope before a species can be correctly identified. The various embodiments of the present invention can include phytoplankton in the following classes and orders discussed below.

1. Class Bacillariophyceae (Diatoms)

Phytoplankton in the class Bacillariophyceae are unicellular algae with siliceous frustules; each half of the frustule consists of a valve and a connecting or girdle band; there are sometimes numerous intercalary bands. The valves are marked in various ways by pores, poroids, knobs, areolae, or ribs. The cytoplasm is concentrated near the outer areas of cell while the inner region contains a large vacuole. There are one or more platelike or many disk-shaped chromatophores usually of a yellowish or greenish-brown color. Storage products are chrysolaminaran and oil droplets. The class Bacillariophyceae is divided into two main orders: *Centrales* and *Pennales*.

The members of the order *Centrales* (Centric diatoms) have concentric or radiating sculpture around a point or points. No raphe or pseudoraphe is present and spontaneous movement does not occur. This order is the most important component of marine phytoplankton, and includes the common marine genera: *Skeletonema, Thalassiosira*, and *Chaetoceros*.

The members of the order *Pennales* (Pennate diatoms) have a sculpture arranged with relation to a longitudinal line. They often possess a raphe or pseudoraphe; many species are capable of spontaneous movement. They are commonly found in the benthos (sediments). Common marine pelagic genera include: *Pseudonitzschia, Thalassionema*, and *Navicula*.

2. Class Dinophyceae (Dinoflagellates)

The phytoplankton in the class *Dinophyceae* usually possess a transverse girdle (cingulum) and a longitudinal furrow (sulcus). The cingulum and sulcus meet on the ventral side. The species are either thecate (armoured) or atheate (naked) depending on whether they have cellulose plates in addition to the cell membrane. They use starch and oil as food reserves (the starch stains darkly with Lugol's iodine). The class Dinophyceae is divided into a number of orders.

The members of the order *Prorocentrales* lack furrows and the flagella are inserted near apical end of the cell. They have theca, which are two large valves with small platelets near the flagellar insertion. The platelets may have spines.

The members of the order *Dinophysiales* have both cingulum and sulcus. The cingulum is displaced towards apical end of cell. They have wings (called lists) lining both furrows; the wing along left side is especially well developed and supported by three ribs. Most species are strongly compressed; and therefore are usually seen in lateral view. They are identified by the size and shape of the cell, ornamentation of plates, and morphology of the left sulcal list.

The members of the order *Gymnodiniales* are naked and therefore do not retain their morphology upon preservation. They are identified by size and general shape, position and path of cingulum and sulcus, apical groove, stripes on surface, number of chloroplasts, and position and shape of the nucleus. The *Gymnodinium* and *Gyrodinium* are separated by relative displacement of cingulum; the displacement is >⅕ cell length in *Gyrodinium*.

The members of the order *Peridiniales* are identified by plate arrangement (the cells must be flattened carefully to remove the cell contents). They have a distinctive pore plate at their apex (which looks somewhat like a pork chop). Some species form distinctive chains (e.g., *Alexandrium catenella*).

The members of the order *Noctilucales* main phase is a large naked cell, often with a tentacle. It includes the common marine genera: *Noctiluca*, and *Kofoidinium*.

The members of the order *Pyrocystales* main phase is a non-motile coccoid cell and reproduction is by a gonyaulacoid or gynmodinoid motile cell. It includes the common marine genera: *Pyrocystis*.

3. Class Raphidophyceae (Chloromonads)

There are less than 20 described species of the class Raphidophyceae. They are chloroplasts discoid that are yellow to yellow brown in color. They are biflagellate having anterior flagellum to pull the cells forward, and a posterior flagellum trailing. Their outer membrane disappears when preserved with Lugol's iodine, which causes the class members to resemble a raspberry in appearance.

4. Class Prymnesiophyceae (Prymnesiophytes/Haptophytes)

These class members in the class Prymnesiophyceae are covered with fine organic scales; composed of calcium carbonate in coccolithophores. There are usually two golden brown chloropasts. They are biflagellate with one haptonema. There are approximately 50 species of *Chrysochromulina* alone. They have a diverse generic array of coccolithophores.

5. Class Dictyophyceae (Silicoflagellates)

The class Dictyophyceae members have numerous discoid golden-brown chloroplasts (in photosynthetic genera). There is a single anterior flagellum. The exterior siliceous skeleton is composed of tubular elements. There are very few species; and include the genera: *Dictyocha*, and *Ebria*.

6. Class Euglenopyceae (Euglenoids)

Phytoplankton in the class Euglenopyceae are pliable, green biflagellates and include the common marine genera: *Eutreptiella*, and *Euglena*.

7. Class Prasinophyceae (Prasinophytes)

Class Prasinophyceae members are primitive precursors to higher green algae. They have one to eight flagella, equal or unequal in length, and a deep flagellar pit is common. They have a single, bowl-shaped chloroplast occupying most of the interior space of the cell. Their principal soluble photosynthetic product is mannitol. Their starch stains reddish-purple or reddish-brown with Lugol's solution. They include the common marine genera: *Pyramimonas, Tetraselmis, Microinonas, Heteromastix*, and *Nephroselmis*.

8. Class Cryptophyceae (Crytomonads)

Phytoplankton in the class Cryptophyceae have tear drop shaped cells, flattened dorso-ventrally. They have two flagella, equal or subequal in length, covered in hairs. Their rectangular or hexagonal surface pattern is evident when using an electron microscope. Usually they have one or two chloroplasts; they also have a broad range of pigmentation (red, blue, olive-yellow, brown, green); some genera are colourless. Their photosynthetic forms store starch that stains darkly when preserved with Lugol's iodine. Their gullet at their flagellar base is lined with ejectosomes. Common marine genera include: *Cryptomonas, Rhodomonas, Plagioselinis, Chroomonas*, and *Hemiselmis*.

9. Class Chrysophyceae (Chrysophytes)

Phytoplankton in the class Chrysophyceae have golden-brown flagellates; usually one or two chloroplasts per cell, some with six. They also usually have two unequal flagella inserted at oblique angle to each other; the larger flagellum is directed forward when swimming, the smaller flagellum is directed towards posterior of cell. Some of them are naked; some have cell coverings of either scales, loricas, or cell walls. Common marine genera include: *Ochromonas, Apedinella, Pseudopedinella*, and *Dinobryon*.

10. Class Chlorophyceae (Chlorophytes)

These class members in the class Chlorophyceae have two or four flagella of equal length, anteriorly inserted in cell (they swim with flagella forward). Most species have a large, cup-shaped chloroplast. Common marine genera include: *Chiamydomonas*, and *Dunaliella*.

As used throughout this document the term "phytoplankton" means the photosynthetic, unicellular organisms belonging to the Kingdom Protista including members of the classes and orders described above.

Figure 2:
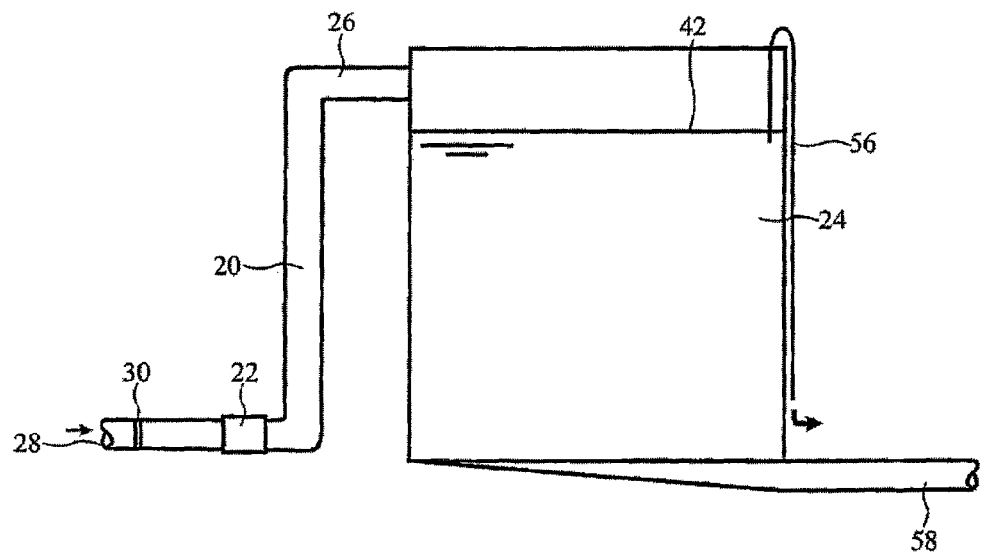
FIG. 2 is a schematic view of the system showing details of a tank.

The phytoplankton is collected from seawater, grown, and harvested to produce an extract. A nutraceutical product is made from the extract. In the process, untreated seawater is collected in storage tanks to obtain the marine phytoplankton. For example, the untreated seawater is retrieved from the Georgia Straight, near Vancouver Island. As illustrated in FIGS. 1 and 2, the untreated seawater is collected in a pipe 20 using a pump 22 and placed in a tank 24. The pipe 20 can be, for example, a 4 foot diameter pipe that is extended out about 1 kilometer from the shoreline. One end 26 of the pipe 20 is connected to the tank 24 and another end 28 of the pipe 20 is positioned about 50 feet to about 90 feet below the surface of the water. For example, the end 28 of the pipe 20 can be about 78 feet below the surface. At this depth, the phytoplankton discussed above can be readily collected. The water collected can be any ambient temperature to grow and harvest the phytoplankton.

The untreated seawater is filtered to remove jellyfish and small pieces of drifting seaweed and other larger multicellular organic material using a filter 30 between the end 28 of the pipe 20 and the tank 24. The filter 30 is designed to pass single cell algae (phytoplankton). This filtered seawater is then pumped through a pipe 20 and into the tank 24 using a pump 22. The pump 22 can be any size to adequately pump the seawater into the tank 24. For example, the pump 22 can be sized to pump 2,000 gallons per minute. The seawater is pumped into the tank 24 until the seawater reaches a desired level in the tank 24. The fill level in the tank 24, for instance, can be set at about 4 to about 5 feet from the top of the tank 24. If the seawater is taken from the waters of the Georgia Straight, near Vancouver Island, it contains large numbers of *Skeletonema, Thalassiosira*, and *Chaetoceros*. This seawater, after filtration, is referred to as "phytoplankton water."

The tanks, such as tank 24, used to store the phytoplankton water are preferably conventional seawater tanks. The tanks can be sized from as little as 20 liters to over 1 million liters. For example, the tanks can include a small tanks of about 2,500 liters, medium tanks of about 5,000 liters, and large tanks of about 850,000 liters. The tank 24 is open to the environment and exposed to natural sunlight. Optionally, growing lights can be used to provide extra light when daylight hours are limited by stormy weather or certain seasons of the year, e.g., winter months.

The phytoplankton collected in this process are "coastal marine temperate species of microalgae." These single-celled organisms range in size from about 1 micrometer up to about 1,000 micrometers (1 mm) and comprise hundreds of species from ten distinct phylogenetic classes, as discussed above. Coastal temperate species of microalgae are generally adapted to eutrophic (high-nutrient) conditions that occur in areas of upwelling. Upwelling transports nutrients from deep water to the surface where light is favorable for photosynthesis. The combination of high light and high nutrients fosters the rapid growth of diatom species from the class Bacillariophyceae. If these conditions remain constant, diatoms will predominate and can eventually form monospecific blooms. However, nature generally provides numerous controlling factors that maintain multispecies mixtures. The species composition at any given time is a result of a complex combination of environmental and biological factors—irradiance, temperature, salinity, ratios of macro-nutrients (principally nitrate, phosphate, and silicate) and micro-nutrients (vitamins, metal cofactors, etc.), circadian rhythms, species interactions (grazing, chemical inhibition, etc.).

Given the complexity, it is understood that the production of such a multispecies mixture has not been successfully achieved on a commercial scale before this process described herein. Most commercial producers of microalgae rely on monospecific cultures. Even growing these on a mass scale presents many logistical problems. The process described herein has developed many control mechanisms to achieve consistent, large-scale, multispecies cultures that essentially mimic nature's powerhouse known as the "diatom bloom."

One factor in achieving the desired growth in the multispecies mixture is the type of nutrients that are used. When the tank 24 is filled with the phytoplankton water, these nutrients are added to assist in the growth of the phytoplankton. These nutrients provide more nourishment than is usually available for the phytoplankton in nature and cause them to rapidly multiply. Preferred nutrients are about 20% phosphoric; about 20% soluble potash; about 0.02% boron; about 0.05% chelated copper; about 0.01% chelated iron; about 0.05% chelated manganese; about 0.0005% molybdenum; about 0.05% chelated zinc; and about 1% ethylenediamine. The rest of the nutrients are typically organic soluble fillers. Other mixtures as known in the art, and variations of the above formula, are also effective to stimulate the phytoplankton growth.

These nutrients are preferably added daily until the phytoplankton reaches concentrations of 50,000 to 5,000,000 cells per milliliter of seawater. Preferably 44 grams of nutrients per ton of seawater are added to the tank daily, although other levels of nutrient may be used. These densities are typically achieved in one to twelve days depending on several variables such as the hours of daylight (or artificial light) that the tank is exposed to and the temperature of the water.

To prevent the algae from settling, falling out, or floating on the surface, or otherwise becoming anaerobic, air is supplied to the tank 24 using a roots type blower or other air system. The roots type blower can be any type of blower to introduce air into the tank 24. For example, the blower can be a high volume, low pressure blower. The air is diffused by air stones, like in a fish aquarium, or a diffuser. The air stones can be placed around the perimeter and middle of the tank 24. This air serves to mix the nutrients and oxygenate the water.

Figure 3:
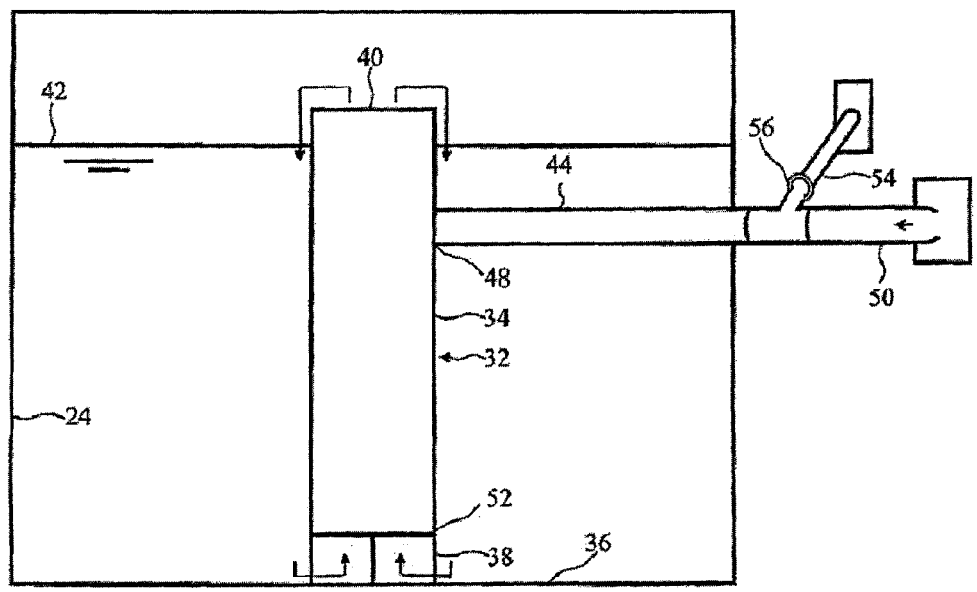
FIG. 3 is a schematic view of the system showing details of a diffuser.

As shown in FIG. 3, a diffuser 32 or aerator is used as an air lift to circulate the water in the tank 24. In this exemplary embodiment, the diffuser 32 includes a mixing chamber 34 placed in the center of the tank 24. The mixing chamber 34, for example, can be made of a 8 inch diameter pipe. The mixing chamber 34 is spaced from the bottom 36 of the tank 24 to provide a space for the phytoplankton water to circulate through the mixing chamber 34 and tank 24. The mixing chamber 34 is spaced from the bottom 36 of the tank 24 using supports 38. For instance, the mixing chamber 34 is spaced from the bottom 36 of the tank 24 about 10 inches using four supports 38. The supports 38 can be made of angle iron, bars, channels, or other members known by one skilled in the art to support a structure above a surface. The top 40 of the mixing chamber 34 is sized to extend above the surface or desired water level 42 about 4 inches.

Air is introduced into the mixing chamber 34 through a line 44. The line 44 can be a 2 inch diameter pipe. A first end 48 of the line 44 is attached to the mixing chamber 34 about ⅓ of the distance down from the top 40 of the mixing chamber 34. A second end 50 of the line 44 is attached to an air source, such as a blower, as discussed above. When air is introduced into the mixing chamber 34, the air mixes with the phytoplankton water to create an air/water mixture and causes the air/water mixture to lift within the mixing chamber 34. The air/water mixture rises above the top 40 of the mixing chamber 34 to spill over the top 40. When the air/water mixture is lifted in the mixing chamber 34, the phytoplankton water is pulled in through the bottom 52; rises up through the mixing chamber 34; and spills over the top 40. This action causes the phytoplankton water to be circulated in the tank 24 and mixed with air, while only causing minimal, if any, damage to the phytoplankton.

The phytoplankton water is checked to verify that the pH balance is within an acceptable range. The pH levels should be between about 4½ to about 8. The optimal level is a pH of about 7½. A second line 54 can be connected to the air intake line 50 to feed $CO_2$ to the phytoplankton water. For example, the second line 54 can be a ¼ inch line connected to the air intake line 50. The second line 54 can be connected to the line 50 using a fitting, such as a tee fitting. A control device 56, such as a valve, can be added to the second line 54 to regulate the amount of $CO_2$ injected into the process. When the density of the phytoplankton increases, the phytoplankton can require more $CO_2$ to maintain the pH balance. A high density, for instance, can be between about 1 million cells per milliliter to about 5 million cells per milliliter. The large tanks usually acquire a higher volume of phytoplankton, which requires adding more $CO_2$. Typically, the night air will introduce enough $CO_2$ in the small tanks to avoid having to manually inject $CO_2$ into the process.

Samples of the phytoplankton are taken from the tank 24 and measured to determine the density of the phytoplankton.

Typically, the phytoplankton water is harvested between about 1½ million cells per milliliter to about 2½ million cells per milliliter. When the phytoplankton water has reached the desired density, food grade NaOH (also known as sodium hydroxide or caustic soda) is added to the phytoplankton water. For example, about 4 lbs. of NaOH is added per ton of algae water. The NaOH causes the cell walls of the phytoplankton to rupture. This process shall be referred to herein as "autolysis." The product produced from this process shall be referred to as "autolysed" or "lysed."

After the NaOH is added, the phytoplankton water in the tank 24 is aerated for another twelve hours or over night. Following the aeration, the tank 24 is then left undisturbed for a further twelve to twenty-four hours to allow the phytoplankton to settle to the bottom of the tank. Then water not containing phytoplankton is drained off using a device such as a siphon 56. The siphon 56 is inserted about two inches from the sediment. Then the water on the top of the sediment is drained over the top of the tank 24, collected, and returned to the ocean.

The water containing the settled phytoplankton is transferred to a filter by draining it through an effluent pipe 58 in the bottom 36 of the tank 24. The bottom 36 of the tank 24 can be sloped to assist drainage of the phytoplankton. For example, the bottom 36 can be sloped at an angle of about ⅛ of an inch to 12 inches. Any remaining sediment can be pushed out of the tank 24 by using a squeegee.

Figure 4:
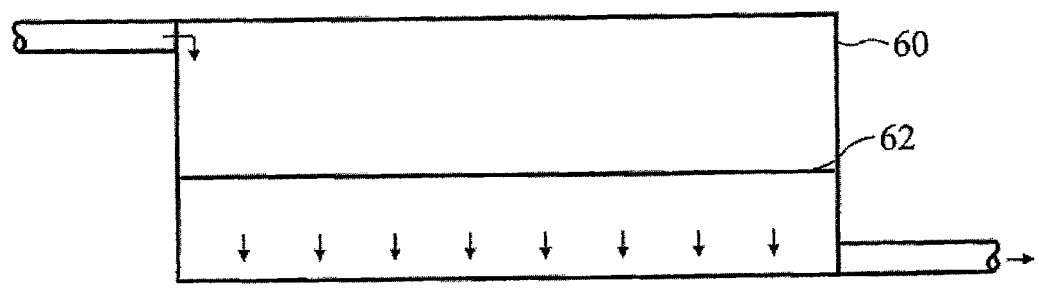
FIG. 4 is a schematic view of the system showing details of a filter.

As shown is FIG. 4, the sediment is placed in a filter 60, such as a gravity filter. The filter 60 includes a filter media 62, for example, a canvas, undyed denim, or like medium. The sediment is precipitated until the water has a moisture content of about preferably about 85% to about 87%, although ranges from 8% to 98% are acceptable (although may require further processing). The phytoplankton water then settles and at this point the phytoplankton water has become an algae paste and is ready for further processing to create powder, liquid or capsules for nutraceuticals or to create a soapy product or liquid for topical applications. The filtered water is returned to the ocean through a return line 64.

The phytoplankton water, before the addition of NaOH, preferably has a pH level of about 8.4. Precipitation of the phytoplankton water should not change the pH level. The addition of the NaOH will raise the pH level of the phytoplankton water to a peak of about pH 10.5 at which point it is buffered by $Mg(OH)_2$. When the NaOH is added to the phytoplankton water, the cell walls rupture causing the inside of the phytoplankton to spill out. This usually occurs within 5 minutes to one hour after the NaOH is added.

A start can be added to a new tank of seawater to help initiate the growing process. The start is taken from another tank having a high culture. The start is usually not needed in a small tank, but is beneficial in a large tank. If a batch, for some reason, does not grow to the desired density, the water is returned to the ocean. Bad batches usually occur every 1 in 12 times. The start improves the probability that the batch will grow to the desired density.

The salt content of the algae paste is about 25 to 32 parts per thousand. However, it is possible to wash the paste to obtain derived products with a salt content of about 2 to 5 parts per thousand. To obtain such products with a low salt content, the algae paste is washed. This is accomplished by placing the algae paste back into the tank from which it was harvested. The tank is then filled with fresh water, and aerated for about twelve hours. The airflow is then shut off and the tank is allowed to settle for twelve hours. The fresh water, which now contains most of the salt from the algae paste, is then drained off. The water and phytoplankton remaining in the tank will have a salt content of about 2 to 5 parts per thousand. This water is pumped through a filter to create an algae paste, which is then precipitated and allowed to settle.

Once the algae paste has settled for twelve hours (either the high or low salt concentrations) it preferably consists of 3 layers: a metallic organic compound soap layer formed from a Mg++ cation, a layer mixing both the soap and the phytoplankton, and a pure phytoplankton layer. The soap can be removed with a scraper preferably having a stainless steel blade ½₀" thick. This soap may be applied to the skin and can be used to treat conditions such as acne, eczema, scar healing, and reduction, the removal of growths and other dermatological conditions.

There is some remaining soap along with some phytoplankton in the second layer beneath the soap layer. This layer is also removed with a scraper and then can be used for skin applications. The third product, the phytoplankton, which is all that remains, contains trace elements such as iodine, vitamins, and various acids, and is useful as a nutraceutical. It can be processed into liquid, capsules or powder for oral ingestion. It can also remain in paste form for topical applications.

The products created by the above-described process have been found to be effective against several diverse medical conditions. For example, there have been cases, where the products have been beneficial in relieving tension, treating acid reflux, promoting weight loss, helping kidney function, increasing energy levels, assisting in treatment of certain types of cancer and aiding in irritable bowel syndrome. The product has shown to be effective when taken orally in 500 mg. capsule form three times a day.

Analysis of the products have shown the following ingredients:

| Component | |
|---|---|
| Ash | 0.03 to 0.75% |
| Carbohydrate | 1 to 35% |
| Iodine | 5 to 50 mcg/g |
| Moisture | 30 to 80% |
| Protein | 0.2 to 30% |
| Sulfur | 0.01 to 3% |

In addition, the following compounds may be found in the finished algae paste and derived products: aluminum, antimony, arsenic, barium, boron, cadmium, calcium, chromium, cobalt, copper, iron, lead, lithium, magnesium, manganese, molybdenum, nickel, potassium, silver, sodium, strontium, thorium, tin, titanium, uranium, vanadium, zinc, and zirconium. Of particular note are the quantities of boron (0.5 to 300 ppm); calcium (1.0 to 5,000 ppm); iron (0.5 to 25 ppm); magnesium (0.02 to more than 10,000 ppm); potassium (0.5 to 4,000 ppm); sodium (1.0 to 15,000 ppm); strontium (0.01 to 75 ppm); and zinc (0.05 to 20 ppm). The other compounds appear in more minute quantities (typically 0.01 to 10 ppm).

While the phytoplankton based nutraceuticals and process for making the same have been described with reference to the specific embodiments described, the descriptions are only illustrative and are not to be construed as limiting the invention. As such, the optimal dimensional relationships for the parts of the exemplary embodiments of the invention can be varied in size, materials, shape, configurations, form, function and manner of operation. The optimal dimensional relationships, use and assembly that are readily apparent to those skilled in the art and all equivalent relationships to the embodiments illustrated in the drawings and described in the specification are intended to be encompassed by the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of making a phytoplankton extract, the method comprising the steps of:
   i.) collecting seawater directly from a sea, wherein the seawater contains multiple species of single-cell phytoplankton ranging in size from 1 µm to 1000 µm;
   ii.) storing the seawater of step i.) in at least one tank;
   iii.) adding nutrients to the seawater of step ii.) to proliferate the multiple species of single-cell phytoplankton to a concentration of 50,000 to 5,000,000 single-cell phytoplankton per milliliter of seawater;
   iv.) circulating the seawater of step iii.);
   v.) mixing air with the seawater of step iv.);
   vi.) adding sodium hydroxide (NaOH) to the tank at ambient temperature to the seawater of step v.) until the seawater reaches a pH of about 10.5 to autolyze the multiple species of single-cell phytoplankton contained therein;
   vii.) collecting the autolyzed phytoplankton of step vi.) to obtain the phytoplankton extract,
   wherein the phytoplankton extract is an algae paste.

2. The method of claim 1, wherein the step of obtaining the seawater directly from the sea comprises collecting the seawater from a depth of about 50 feet to about 90 feet below the surface of the sea.

3. The method of claim 1, wherein the step of obtaining the seawater directly from the sea comprises collecting the seawater from a depth of about 78 feet below the surface of the sea.

4. The method of claim 1, wherein the step of circulating the seawater comprises using a diffuser to circulate the seawater.

5. The method of claim 4, wherein the step of circulating the seawater with the diffuser further comprises introducing air into the diffuser.

6. The method of claim 1, wherein the step of collecting the phytoplankton comprises filtering the phytoplankton from a portion of the seawater.

7. The method of claim 1, further comprising a step of exposing the seawater in the tank obtained directly from the sea to direct sunlight.

8. The method of claim 1, further comprising a step of adding carbon dioxide ($CO_2$) to the air in the step of mixing air.

9. The method of claim 1, further comprising a step of settling the phytoplankton from the seawater to provide settled phytoplankton.

10. The method of claim 9, further comprising a step of draining the seawater from the settled phytoplankton.

11. The method of claim 1, further comprising a step of processing the algae paste into a powder.

12. The method of claim 1, further comprising a step of processing the algae paste into a liquid.

13. The method of claim 1, wherein the phytoplankton wherein the multiple species of single-cell phytoplankton comprise phytoplankton from one or more classes selected from the group consisting of: class Bacillariophyceae, class Dinophyceae, class Raphidophyceae, class Prymnesiophyceae, class Dictyophyceae, class Euglenopyceae, class Prasinophyceae, class Cryptophyceae, class Chrysophyceae, and class Chlorophyceae.

* * * * *